(12) United States Patent
Ansley

(10) Patent No.: US 10,446,008 B2
(45) Date of Patent: *Oct. 15, 2019

(54) GAS-MONITORING APPARATUS FOR DETECTING BOWEL MOVEMENTS AND METHOD OF USE

(71) Applicant: Sensor Technologies, LLC, Lawrence, KS (US)

(72) Inventor: Brad W. Ansley, Shawnee, KS (US)

(73) Assignee: Sensor Technologies, LLC, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/955,348

(22) Filed: Apr. 17, 2018

(65) Prior Publication Data

US 2018/0233020 A1    Aug. 16, 2018

Related U.S. Application Data

(63) Continuation of application No. 15/615,483, filed on Jun. 6, 2017, now Pat. No. 9,947,203, which is a
(Continued)

(51) Int. Cl.
*G08B 21/12* (2006.01)
*H04N 7/18* (2006.01)
(Continued)

(52) U.S. Cl.
CPC .............. *G08B 21/12* (2013.01); *A61F 13/42* (2013.01); *G01N 27/407* (2013.01);
(Continued)

(58) Field of Classification Search
CPC .................. G01N 27/407; G01N 33/48; G01N 2033/4977; A61B 5/6887–6898; A61B 5/42
(Continued)

(56) References Cited

U.S. PATENT DOCUMENTS 9,947,203 B2 * 4/2018 Ansley .................. G08B 25/08
2006/0061477 A1   3/2006 Yeh
(Continued)

FOREIGN PATENT DOCUMENTS

JP      2000245779      9/2000
KR      20090119157     11/2009
(Continued)

OTHER PUBLICATIONS

"Extended European Search Report", EPO Application No. 16275013.7, dated May 27, 2016.
(Continued)

*Primary Examiner* — Daryl C Pope
(74) *Attorney, Agent, or Firm* — Law Office of Mark Brown, LLC; Christopher M. DeBacker

(57) ABSTRACT

A room monitoring device designed and intended to detect a bowel movement (BM) of a person occupying the room, such as a baby or infant or an adult with special needs or in a care facility. The device tests the air for particular substances such as, but not limited to, methane and hydrogen sulfide. The test is performed multiple times per minute to reduce the chances of a false-positive detection. Once the device detects a positive BM, it alerts a user via Wi-Fi message, SMS text message, visual alerts (e.g., flashing lights), and/or audio alerts. This device may be paired with existing monitoring devices, such as a baby monitor with a remote camera.

15 Claims, 9 Drawing Sheets

Related U.S. Application Data continuation-in-part of application No. 14/606,494, filed on Jan. 27, 2015, now Pat. No. 9,671,383.

(60) Provisional application No. 61/931,880, filed on Jan. 27, 2014.

(51) Int. Cl.
| | |
|---|---|
| *G01N 33/00* | (2006.01) |
| *A61F 13/42* | (2006.01) |
| *G01N 27/407* | (2006.01) |
| *G01N 33/497* | (2006.01) |
| *G08B 25/08* | (2006.01) |
| *G01N 27/416* | (2006.01) |
| *A61B 5/00* | (2006.01) |

(52) U.S. Cl.
CPC ....... *G01N 27/416* (2013.01); *G01N 33/0016* (2013.01); *G01N 33/0031* (2013.01); *G01N 33/0062* (2013.01); *G01N 33/0075* (2013.01); *G01N 33/497* (2013.01); *G08B 25/08* (2013.01); *H04N 7/185* (2013.01); *A61B 5/6889* (2013.01); *A61B 5/6891* (2013.01); *A61F 2013/424* (2013.01); *G01N 2033/4975* (2013.01)

(58) Field of Classification Search
USPC .............. 340/506, 3.1, 511, 517, 521, 539.1, 340/539.11, 539.13
See application file for complete search history.

(56) References Cited

U.S. PATENT DOCUMENTS

| | | |
|---|---|---|
| 2008/0208016 A1 | 8/2008 | Hughes et al. |
| 2013/0110061 A1 | 5/2013 | Abraham et al. |
| 2014/0333442 A1 | 11/2014 | Carney |
| 2015/0212034 A1 | 7/2015 | Ansley |
| 2015/0330958 A1 | 11/2015 | Carney et al. |

FOREIGN PATENT DOCUMENTS

| | | |
|---|---|---|
| WO | 2012126507 | 9/2012 |
| WO | 2014098691 | 6/2014 |

OTHER PUBLICATIONS

"RAE Sytems Technical Note", RAE Systems Tehcnical Note TN-114 rev 16 wy/wh. 11-04, believed published Nov. 2004, downloaded Aug. 19, 2017 from http://ecoenvironmental.com.au/wp-content/uploads/gas_VRAE_Sensor Specs_and_Cross_Sensitivities.pdf.

* cited by examiner

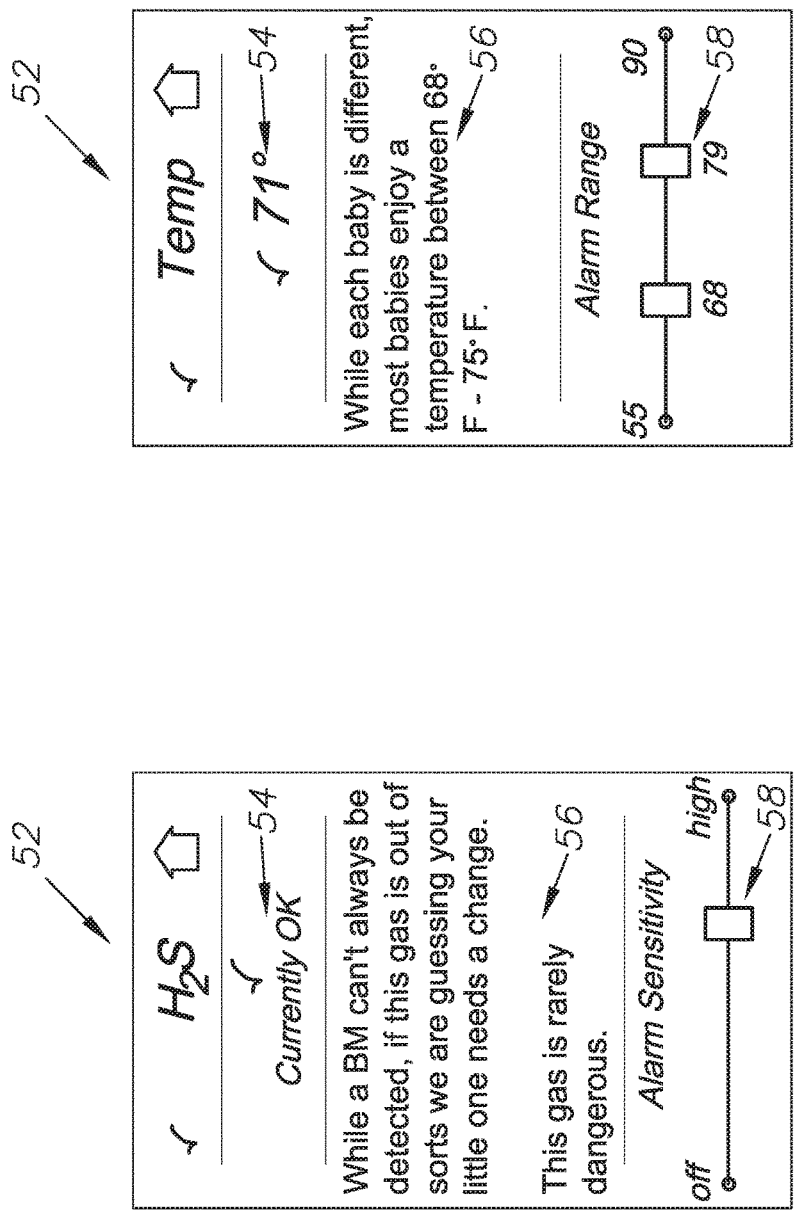

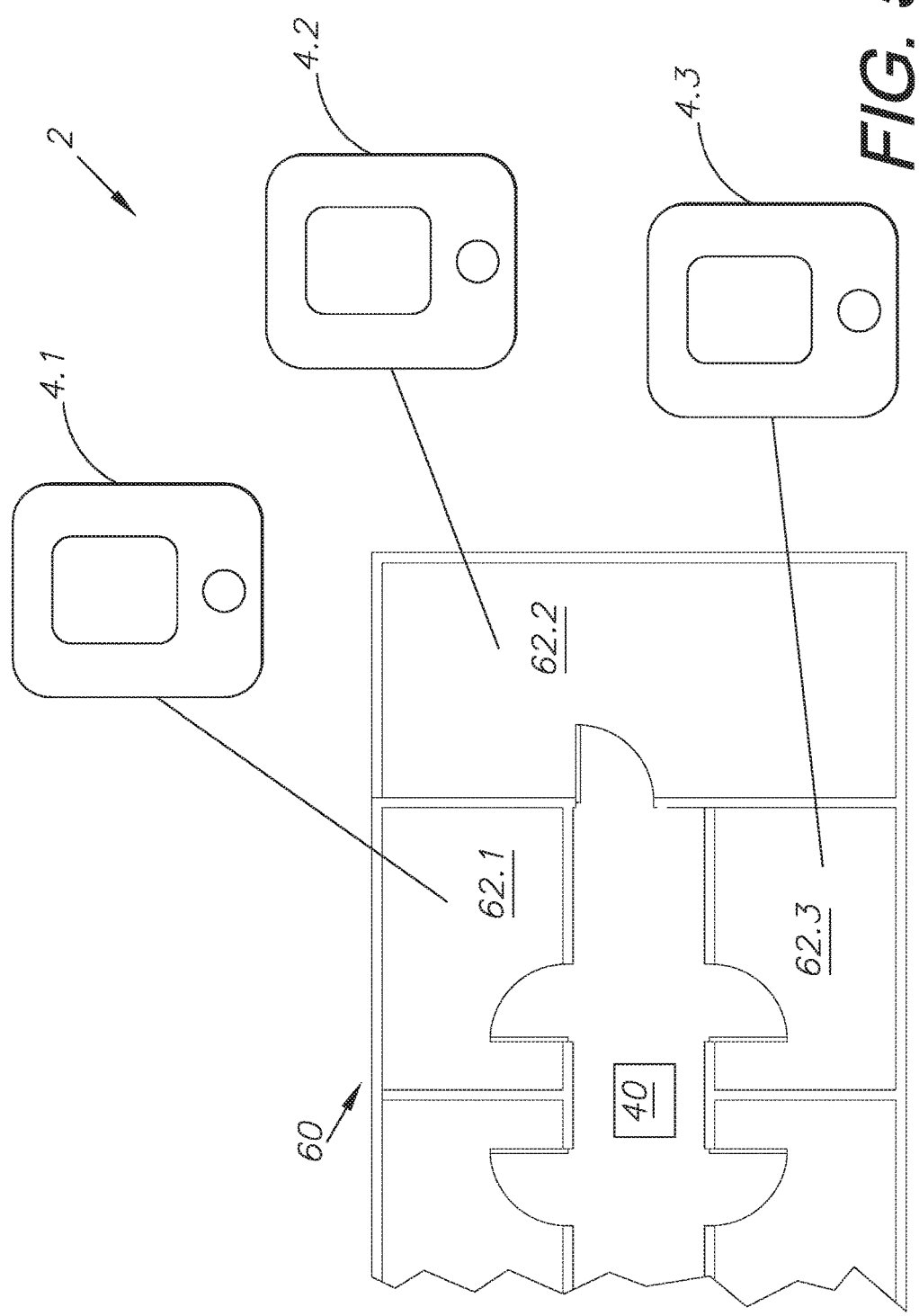

GAS-MONITORING APPARATUS FOR DETECTING BOWEL MOVEMENTS AND METHOD OF USE

CROSS-REFERENCE TO RELATED APPLICATION

This application is a continuation of and claims priority in U.S. patent application Ser. No. 15/615,483, filed Jun. 6, 2017, which is a continuation-in-part of and claims priority in U.S. patent application Ser. No. 14/606,494, filed Jan. 27, 2015, now U.S. Pat. No. 9,671,383 which claims priority in U.S. Provisional Patent Application No. 61/931,880, filed Jan. 27, 2014, all of which are incorporated herein by reference.

BACKGROUND OF THE INVENTION

1. Field of the Invention

The present invention relates generally to a gas monitoring apparatus, and more specifically to an apparatus for monitoring humans, such as babies and infants, for bowel movements while they sleep using gas detecting elements.

2. Description of the Related Art

Often children wake crying during the night. This is often caused by a bowel movement (BM) happening during the night, and diaper rash or other discomforts can wake the child. It is impossible for a parent to know whether the child needs to have their diaper changed without physically checking the diaper for a BM. This can be detrimental when the child is crying for no reason, but the parent is forced to wake and check the child anyway.

Older adults in care or special needs patients would similarly benefit from a passive monitoring device to alert healthcare workers when the patient has suffered a BM. The worker would be alerted and could aid the patient to prevent bed sores etc.

What is needed is a method of actively monitoring a sleeping child and indicating if a bowel movement has occurred through the use of sensors which prevents unnecessary checking of diapers.

Heretofore there has not been available a system or method for detecting bowel movements with the advantages and features of the present invention.

BRIEF SUMMARY OF THE INVENTION

The present invention generally provides a sensor apparatus for detecting gasses associated with bowel movements, such as, but not limited to, methane or hydrogen sulfide. In a preferred embodiment, the detector will take multiple samples over a desired time period to avoid false positives. The sensor apparatus is capable of alerting parents or others when a bowel movement is detected via sounds, lights, wireless messages to a mobile device, or other means. This allows the sensor apparatus to be paired with other existing products (e.g., baby monitoring systems) without requiring additional equipment.

BRIEF DESCRIPTION OF THE DRAWINGS

The drawings constitute a part of this specification and include exemplary embodiments of the present invention illustrating various objects and features thereof.

FIG. 1 is a diagrammatic representation of a preferred embodiment of the present invention and elements with which it can communicate through.

FIG. 3 is a diagrammatic representation of a sample status screen of a graphical user interface associated with the present invention.

FIG. 4 is an alternative representation thereof.

FIG. 5 is a diagrammatic representation of a floorplan having an embodiment of the present invention installed throughout.

DETAILED DESCRIPTION OF THE PREFERRED EMBODIMENTS

I. Introduction and Environment

Figure 1:
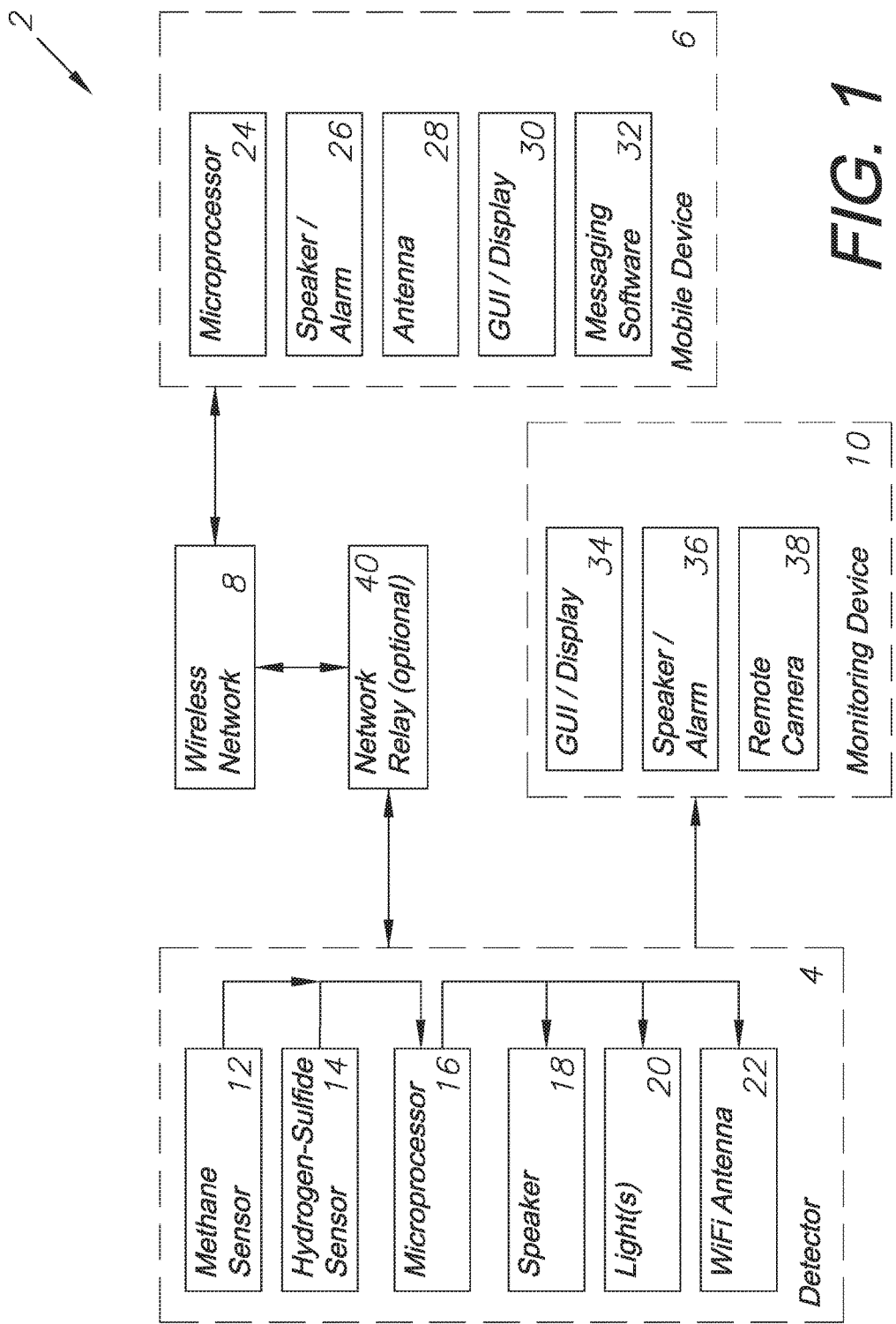

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Additional examples include a mobile smart device including a display device for viewing a typical web browser or user interface will be commonly referred to throughout the following description. The type of device, computer, display, or user interface may vary when practicing an embodiment of the present invention. Said terminology will include the words specifically mentioned, derivatives thereof and words of similar meaning.

Gasses associated with bowel movements which would trigger the present invention include, but are not limited to: Indole ($C_8H_7N$), 3-methylindole ($C_9H_9N$), hydrogen Sulfide ($H_2S$), Amines, Ethanoic Acid ($C_2H_4O_2$), Butyric Acid ($C_4H_8O_2$), and methane ($CH_4$). These compounds are included amongst a number of outputs from human solid waste. For the purposes of the present application, any or all of these outputs should be considered to be used or to be detected for by the sensor system embodying the present invention.

Two types of gaseous sensor systems exist in the market place: (1) electrochemical sensors; and (2) metal oxide semiconductor (MOS) sensors. Either sensor type could be used in an embodiment of the present invention; however an MOS sensor is utilized in the preferred embodiment. The preferred sensor, MiCS-5524, is capable of measuring and detecting volatile organic compounds in a relative manner, such as by detecting changes in the environment, which provides an output of resistance change. The sensor can measure virtually any reducing and/or aromatic gas: such as: ammonia, carbon monoxide, hydrogen sulfide etc., as well as any compound mentioned above. The MOS sensors are combusted by the presence of reducing gases at the sensor surface, and the release of electrons from these gases causes resistance across the sensor plate to drop.

Odors from human waste relate to foods eaten, not age. The emissions are essentially the same between infants and adults, but the present application focuses our technology on the most common denominator: hydrogen sulfide, but other gasses must also be tested for. As is well known, infants less than 6 months that are breast feeding do not emit much if any odor. Detecting latent odorless gasses would be highly beneficial to the purpose of the present invention.

II. Preferred Embodiment Bowel Movement (BM) Sensor System 2

Referring to the figures in more detail, FIG. 1 shows a diagrammatic representation of a preferred BM sensor system 2, including a BM sensor/detector 4 for detecting a BM based upon gasses in the room, a mobile device 6 for receiving alerts from the BM sensor, and a wireless network 8 over which the mobile device 6 and the detector/sensor 4 communicate.

The detector 4 can also be used in conjunction with standard monitoring devices 10, such as a baby monitor with audio and/or video surveillance. Similarly, the detector 4 may access the wireless network 8 directly, or it may interact with a network relay 40 device for communicating between the network 8 and the detector 4. Alternatively, the relay 40 may only allow direct communication between the mobile device 6 and the detector 4, wherein other network access is limited or cut off.

As shown, the detector 4 includes sensors for detecting gas within the room, such as a methane sensor 12, a hydrogen sulfide sensor 14, or other sensors capable of detecting gasses which are emitted as part of solid or liquid human waste for detection with the BM detector 4. A microprocessor 16 receives data from the sensors 12, 14 and determines whether or not an alert should be sounded based upon preset or predetermined thresholds. The microprocessor can facilitate an alert by creating a noise amplified through a speaker 18, by flashing one or more lights 20 located on the detector 4, or by sending a wireless alert to the mobile device 6 using a Wi-Fi antenna 22 or other means of communication with the mobile device 6.

To increase the range of notifications, the audio or visual alerts created by the detector 4 through the use of the speaker 18 or the lights 20, respectively, a monitoring device 10 can be used. This monitoring device may or may not include a graphical user interface 34, a separate speaker or alarm 36 for the audio alert, and a remote camera 38 for the visual alert. This monitoring device 10 could be a standalone baby monitoring system to alert a parent if the baby is crying or not sleeping.

The mobile device 6, such as a standard smartphone device, includes a separate microprocessor 24, a speaker 26, an antenna 28, a graphical user interface (GUI) 30, and messaging software 32. The GUI may be a touchscreen interface, and may allow the user to directly make changes to the settings of the detector 4 using wireless access through software. The messaging software may include typical SMS messages sent using a service associated with the detector 4, or a completely separate software application or APP downloaded from a wireless network for use specifically with the detector 4.

Figure 2:
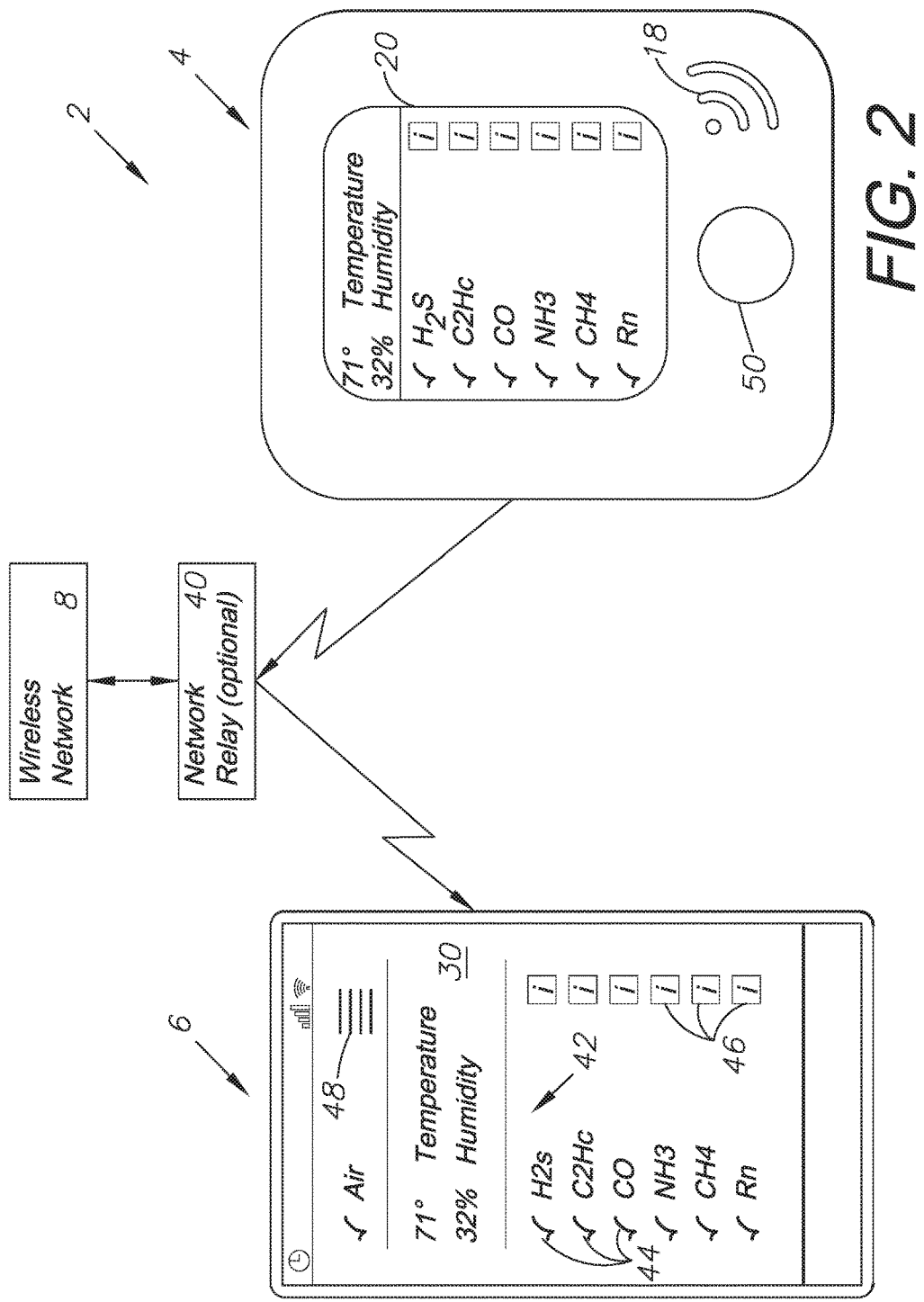
FIG. 2 is a diagram showing a simple relationship between various components of an embodiment of the present invention.

FIG. 2 shows a relationship between the mobile device 6 and the detector 4. The detector shown here includes controls 50 for accessing the settings of the detector directly. These settings can also be controlled wirelessly using the mobile device 6. A typical GUI 30 display screen on the mobile device includes such features as: ambient status 42 of the room being monitored; alert statuses 44 associated with various chemical compounds typically associated with a BM; information "buttons" 46 for accessing information about each substance or air quality value being detected for; and a settings pulldown button 48 for choosing different views or altering software settings of the mobile device 6 or of the detector 4.

The detector 4 may include controls 50 which allow direct access to the software or hardware settings of the detector. A speaker 18 located somewhere on the body of the detector delivers audio alerts, while a display or light 20 delivers visual alerts. Here, the GUI is also shown to include settings information that may be accessible via the mobile device 6. The GUI could simply flash when an alert is detected, may display the settings of the detector, or may otherwise give visual alerts to the user.

FIGS. 3 and 4 are examples of GUI display screens 52 that may be accessible via the mobile device 6 or the display portion of the detector 4. FIG. 3, for example, shows the information status of H2S (Hydrogen Sulfide) being detected in the room by the detector 4. This display screen may be accessed by selecting the information button 46 associated with H2S on a home screen as shown in FIG. 2.

The status 54 of the selected element or room factor (e.g., temperature, gas presence, humidity) is displayed prominently, along with a checkmark or other indicator that everything is normal, or another indicator if the levels of the selected room factor or element are outside the set parameters. The parameters may be set using a scrolling bar 58 for determining when the alarm will be triggered by that room factor, if at all. A description of the element or room factor being reviewed is shown at 56. FIG. 4 shows a similar display, using air temperature as an example. Here, the sliding bar 58 includes an upper range and a lower range, allowing the user to customize that particular room factor even further.

FIG. 5 shows a floorplan 60 for a building, such as a home, hospital, or healthcare facility. Three rooms 62.1, 62.2, 62.3 are displayed, and three detectors 4.1, 4.2, and 4.3 are placed in the rooms respectively. A central relay 40 relays all data received from the detectors 4.1, 4.2, 4.3 to a stationary or mobile computing device, or multiple devices, to alert staff of a BM or other room irregularity. This setup is particularly useful in an adult care facility.

Figure 6:
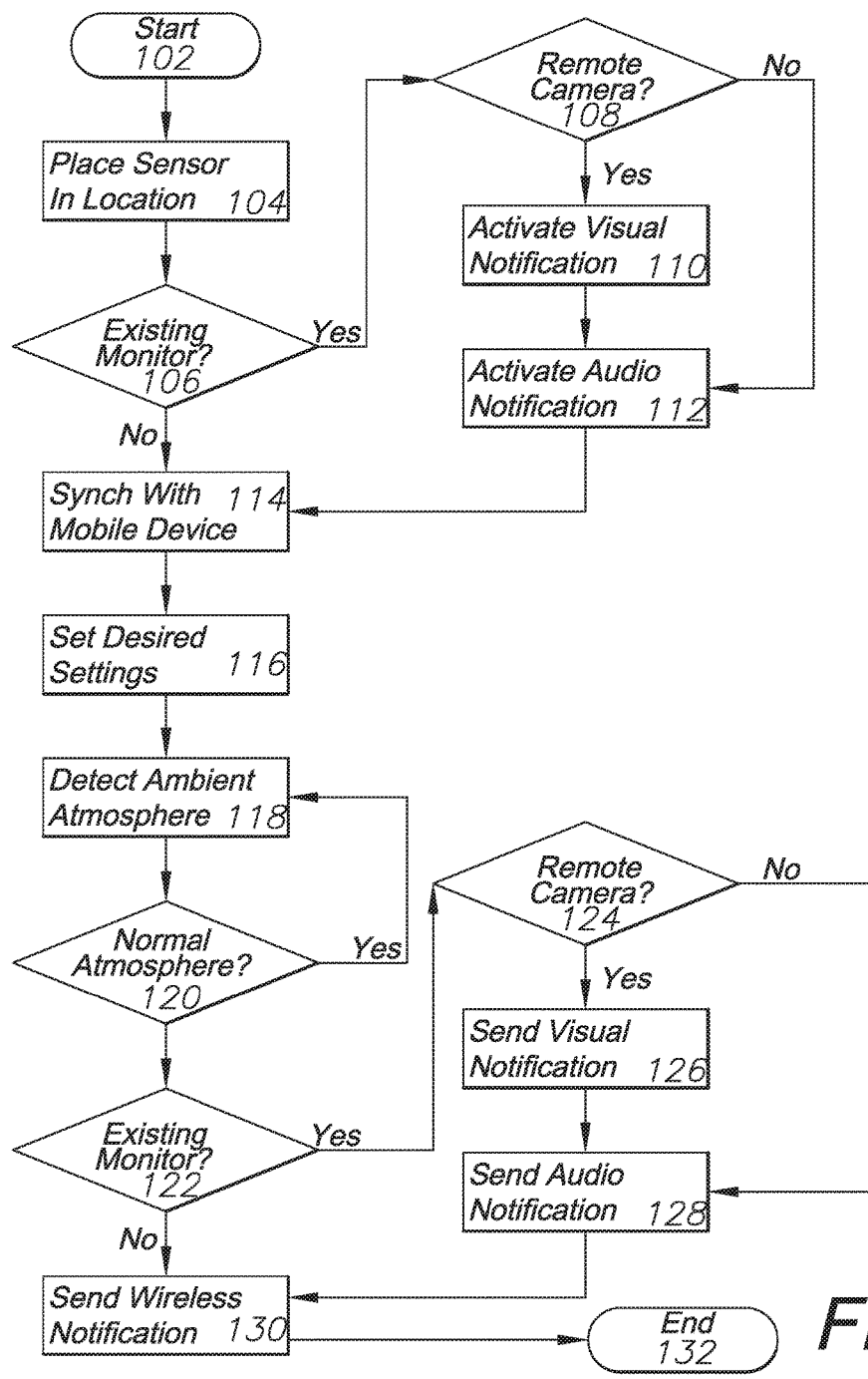
FIG. 6 is a flowchart diagramming the steps taken in practicing and embodiment of the present invention.

FIG. 6 is a flowchart demonstrating some steps taken while practicing a preferred embodiment of the present invention. The process starts at 102. A sensor is placed in a location at 104, preferably in a child or patient's room where a BM may occur while that person is sleeping. A check is performed at 106 whether an existing room monitoring device, such as a baby monitor, exists.

If an existing room monitoring device exists at 106, there is a determination at 108 if there is also a remote video camera associated with the existing room monitoring device. If yes, then the visual notification feature of the sensor is activate at 110. Either way, an audio notification is activated at 112.

Regardless of whether an existing monitor exists or not at 106, the sensor device is synched with one or more mobile computing devices at 114. This allows alert messages or other communication to be sent from the sensor/detector device and the mobile device(s). The user may also set desired settings 116 of the detector using the mobile computing device or the detector itself. These settings are the preferences for how sensitive the detector will be, and will be the basis for the ambient room atmosphere.

After this is all setup, the sensor actively monitors the ambient atmosphere of the room at 118. A check is constantly performed at 120 to determine whether the ambient room factors are within normal levels. If yes, then the cycle continues.

Once an abnormality is determined at 120, alert notifications must be sent out by the sensor device. If there is an existing monitoring device at 122 and a remote camera is present at 124, then the sensor will flash, light up, or otherwise activate a visual display that can be seen via a remote monitoring device connected to the remote camera at 126. At the same time, audio alerts, such as beeps or buzzing noise, will be produced by the sensor device at 128. This also will be sent through the monitoring device and played on a speaker associated with the existing monitoring device.

At the same time, or if there is no exiting monitor in place, a wireless notification is sent to the mobile device(s) associated with the sensor/detector at 130. These notifications may be sent via SMS messaging, or software specifically associated with the sensor/detector device, or through other means (e.g., automated telephone call). Once all alerts are sent, the process ends at 132. The process may automatically revert to a detection of ambient atmosphere at 118 once the issues associated with the alert have been addressed, or the system may require manual reset.

III. Alternative Embodiment Event Sensor System 202

Figure 7:
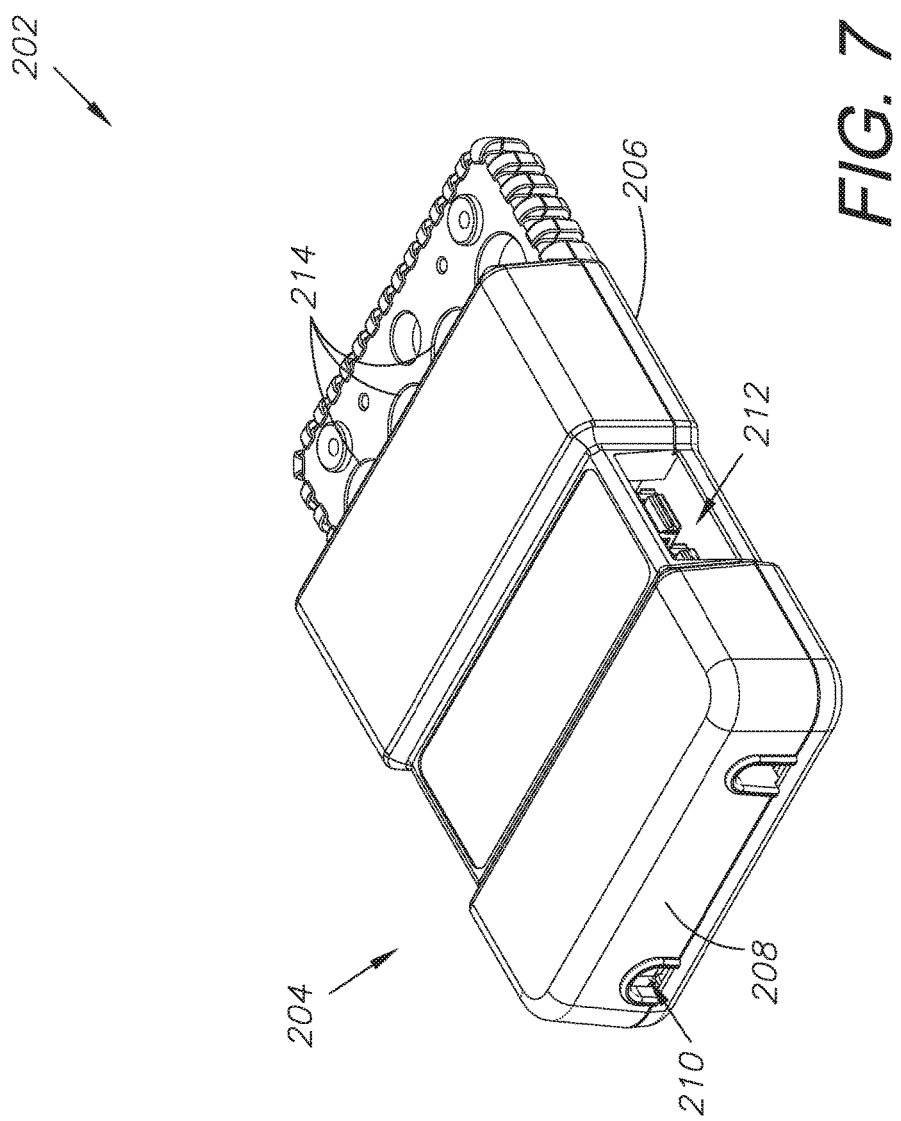
FIG. 7 is a three-dimensional isometric view of an alternative embodiment of the present invention.
Figure 8:
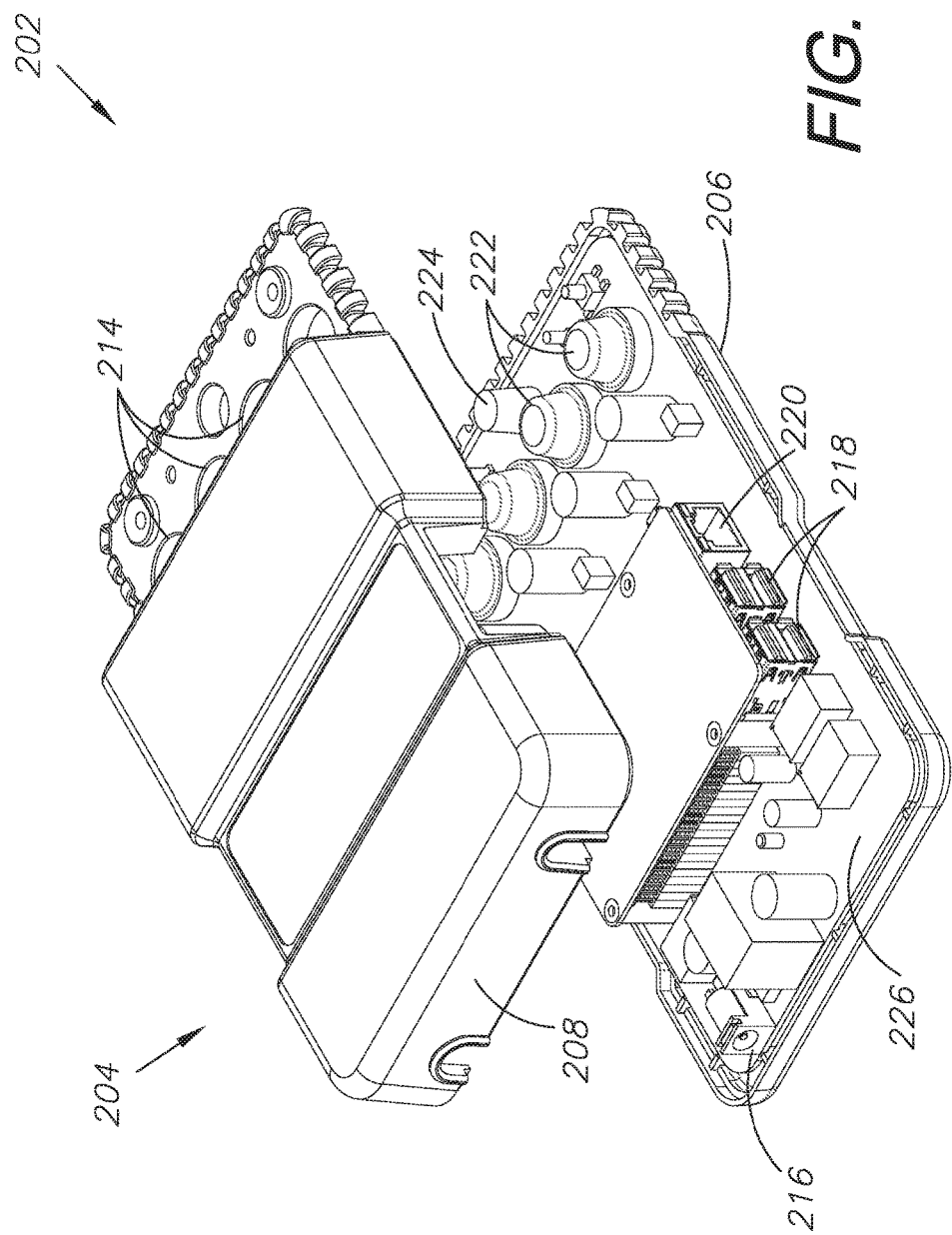
FIG. 8 is an exploded three-dimensional isometric view thereof.
Figure 9:
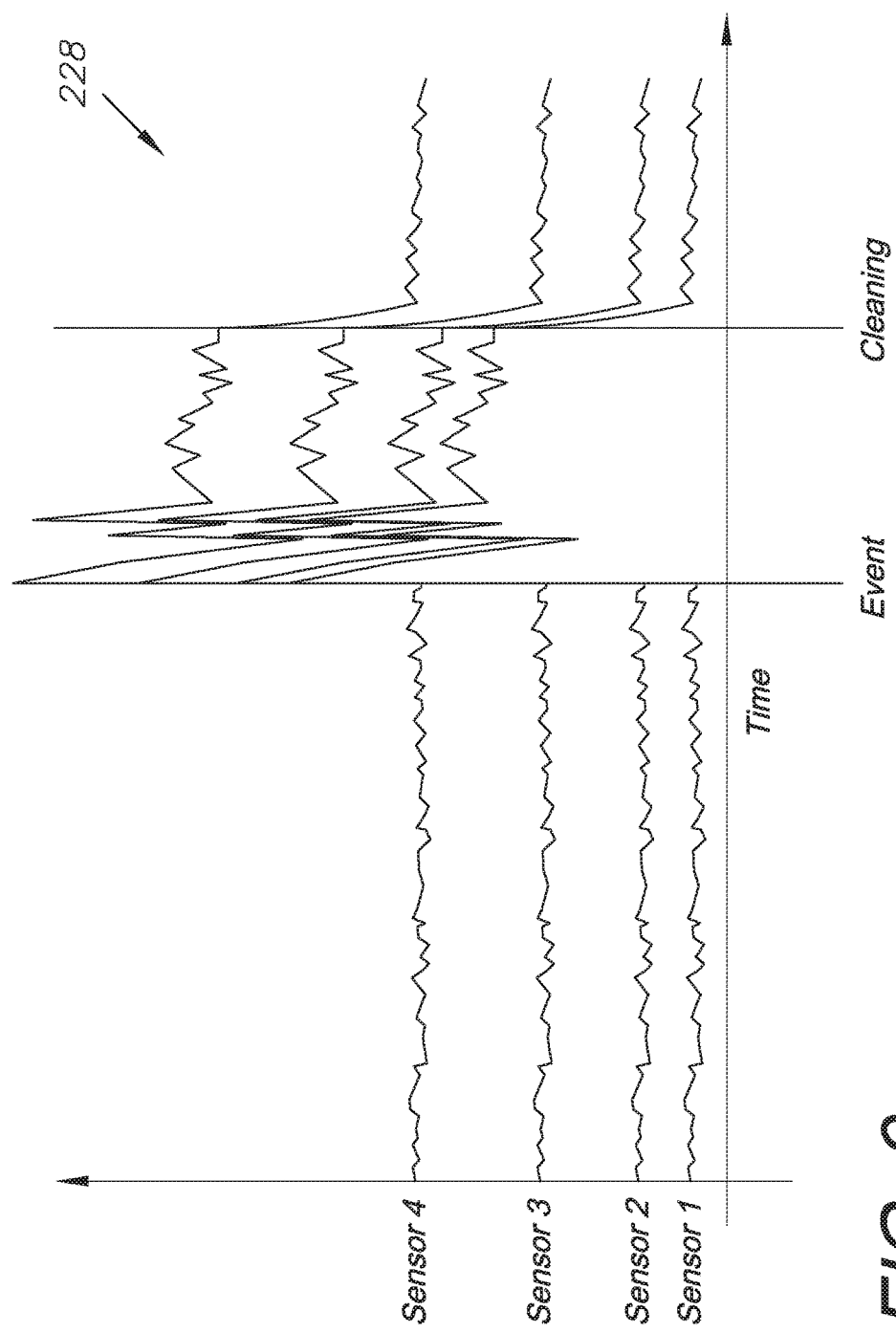
FIG. 9 is diagrammatic chart showing the profile of an event associated with the embodiment thereof.

FIGS. 7-9 show an alternative embodiment event sensor system 202, which uses an event sensor 204 to detect an event, such as a fecal event, urine event, emesis, or other important event in a space, and can determine whether cleaning or other immediate response is necessary.

Primarily, this system 202 could be used in hospitals, nursing homes, or could even be adapted for use in nurseries or for home use. The sensor 204, as shown in FIGS. 7 and 8, includes a bottom housing 206 and a top housing 208. The top housing has a power port opening 210 for receiving power at a power input 216, a data connection opening 212 for receiving data connection cables, such as USB ports 218 and networking or Ethernet cable port 220 (e.g. Category 6 connector). The top housing also contains openings 214 for various gas sensors 222 and a motion sensor 224 for detecting elements of an event. The sensors 222, 224, USB ports 218, Ethernet port 220, power input 216, and all relevant components are mounted to a printed circuit board (PCB) 226 within the top 208 and bottom 206 housing. Each gas sensor 222 includes a heating element for igniting and detecting various chemical elements.

The four gas sensors 222 detect various chemical elements which, when sensed in specific amounts, will indicate a specific event has triggered. A first gas sensor may sense IAQ Ammonia, sulfide, and benzene. A second gas sensor may sense Hydrogen Sulfide. A third gas sensor may sense Ammonia. A fourth gas sensor may sense VOC Gas (e.g. Alcohol, Toluene, and Acetone). In a preferred embodiment, however, as shown in FIG. 9, each gas sensor 222 detects a broadband of gasses with varying selectivity. Each are not specific to a single gas species but are optimized for different applications. This allows for a more accurate determination of when an event occurs. Coupled with a motion sensor 224, temperature sensor, and humidity sensor, a specific event can be detected for, resulting in assigning an appropriate response and alerting the proper crews what sort of event they need to prepare for cleaning and servicing the patient.

Through use and testing using this combination of sensors, specific profiles have been determined for various events, including fecal event, urine event, or emesis.

FIG. 9 shows the occurrence of an "event" as detected by one or more of the various sensors. The sensors detect various chemicals, and based on the profile 228 of the detected event amongst the various sensors, the sensor system can determine what type of event has occurred, which directly leads to what type of response is required. In addition to the gas sensors 222, and motion sensor 224, there are temperature and humidity sensors which detect temperature and humidity in the vicinity of the patient or occupant. Tests have shown that both temperature and relative humidity increase at the time of an event and decrease significantly after cleaning. Each of the four gas sensors 222 detect multiple gasses of various profiles, each optimized for different applications. As shown in FIG. 9, each of the four sensors is reporting different levels of response, but the variances would indicate what type of event has occurred. In an embodiment, the four sensors could include one MQ135 sensor, one MQ136 sensor, one MQ137 sensor, and one MQ138 sensor. In addition, relative humidity and changes in temperature would also add to the generation of the profile.

Figure 10:
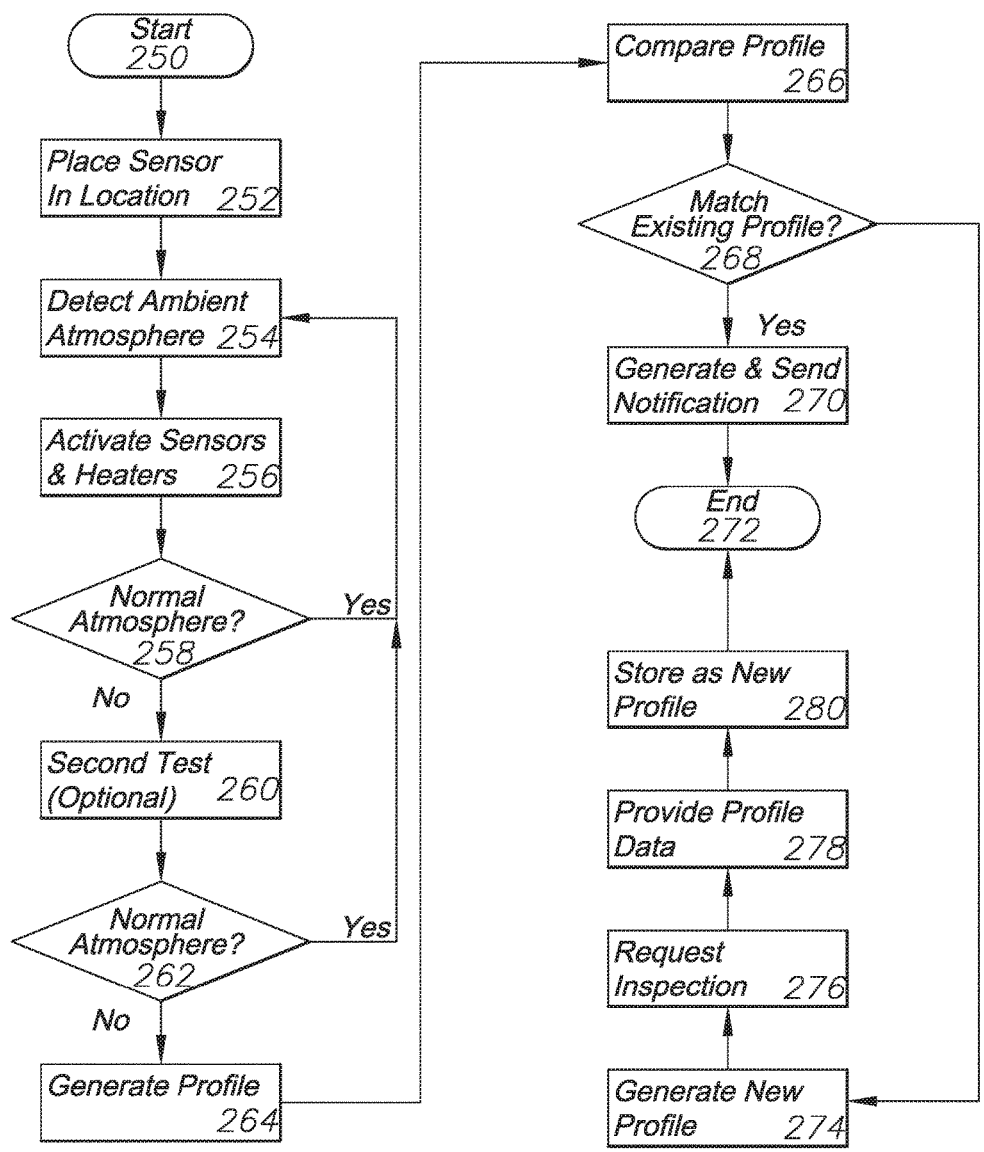
FIG. 10 is a flowchart diagramming the steps taken in practicing a method of the present invention.

FIG. 10 shows a flowchart stepping through the process of practicing this embodiment of the present invention. The process starts at 250. As before, the sensor is placed in location 252, such as in a room or in the vicinity of a patient/subject. The sensor beings detecting the ambient atmosphere at 254, and the sensors and heaters are activated at 256, thereby detecting temperature, humidity, movement, gas levels, and other various attributes of the surroundings of the sensor.

As long as normal atmosphere is detected at 258, the monitoring of the room continues. If abnormal atmosphere is detected at 258, a second, optional testing is done at 260. If this second test determines a false alarm at 262, monitoring continues at 254. However, if the second test confirms abnormal atmospheric conditions at 262, a profile is generated at 264. That profile is based on all sensor data, including motion, temperature, humidity, and gas and particle detection levels.

At 266, the generated profile is compared with existing known profiles to determine if the event is a known type of event. If a matching profile is detected at 268, the sensor system generates and sends an appropriate notification to the user at 270 and the process ends at 272 with the user responding to the event appropriately.

If a mating profile is not detected at 268, that means that the sensor has detected something abnormal, but it is not recognized based on its profile as any known even type. A new profile is then generated at 274, and a request for inspection of the room is sent at 276. Someone must inspect the room and determine what the event is, and provide profile data at 278 to the new profile. This may be identifying this new profile with a previously known event, or by creating an entirely new event-type that wasn't previously being monitored for by the system. The new profile is stored at 280 for future reference, and the process ends at 272.

All of the potential evens have specific atmospheric profiles that can be measured by the sensor(s) in real time. Information can be stored locally and/or sent to an offsite server for analysis, review, and then can be presented to the user via a web interface or some other display means, allowing, for example, hospital or nursing home staff to view, customize, and report event data.

It is to be understood that while certain embodiments and/or aspects of the invention have been shown and described, the invention is not limited thereto and encompasses various other embodiments and aspects.

The invention claimed is:

1. An event detector system for placement in an occupied room, the system comprising:
   an event detector comprising a housing, a microprocessor, a first gas sensor, a second gas sensor, a motion sensor, a temperature sensor, and a humidity sensor;
   said first gas sensor comprising a broadband gas sensor calibrated at a first broadband gas spectrum;
   said second gas sensor comprising a broadband gas sensor calibrated at a second broadband gas spectrum;
   each of said first and second gas sensors connected to a heater element for vaporizing and detecting said respective first and second broadband gas spectrums;
   said microprocessor configured to receive sensor information from said first gas sensor, said second gas sensor, said motion sensor, said temperature sensor, and said humidity sensor;
   said microprocessor further configured to generate a profile based upon said sensor information;
   said microprocessor further configured to compare said profile to known profiles and to make a determination whether an event has occurred; and
   said event detector further comprising a notification device configured for sending a notification upon determination of whether an event has occurred.

2. The system of claim 1, wherein said respective first and second broadband gas spectrums contain substances chosen from the list comprising: Indole (C8H7N), 3-methylindole (C9H9N), hydrogen Sulfide (H2S), Amines, Ethanoic Acid (C2H4O2), Butyric Acid (C4H8O2), Ammonia, sulfide, benzene, Ammonia, Alcohol, Toluene, Acetone, and methane (CH4).

3. The system of claim 1, wherein said first and second gas sensors are electrochemical sensors.

4. The system of claim 1, wherein said first gas sensor is a metal oxide semiconductor (MOS) sensor.

5. The system of claim 1, further comprising:
   said first gas sensor and said second gas sensor are configured to test said respective first broadband gas spectrum and said second broadband gas spectrum at least twice over a predetermined time period; and
   wherein an alert is generated upon positive detection of said respective first and second broadband gas spectrums at each test over said predetermined time period.

6. The system of claim 1, further comprising:
   said mobile computing device including a software program including a user interface configured to relay information from said event detector to the user;
   said software program comprising a messaging application configured to receive alert messages from said event detector; and
   said software program further comprising an interface application for adjusting a plurality of range settings associated with said event detector.

7. The system of claim 6, wherein said range of settings associated with said event detector are selected from the list comprising: Indole (C8H7N) levels, 3-methylindole (C9H9N) levels, hydrogen Sulfide (H2S) levels, Amine levels, Ethanoic Acid (C2H4O2) levels, Butyric Acid (C4H8O2) levels, methane (CH4) levels, ambient temperature, and humidity.

8. The system of claim 7, further comprising an adjustable upper range limit for said range of settings, said adjustable upper range limit adjustable using said software program of said mobile computing device.

9. The system of claim 8, further comprising an adjustable lower range limit for said range of settings, said adjustable lower range limit adjustable using said software program of said mobile computing device.

10. The system of claim 1, further comprising:
    a room monitoring system comprising a microphone and a remote monitoring device comprising a speaker, said remote monitoring device configured to receive audio communications from said monitoring system microphone;
    said event detector comprising a speaker configured to produce an audible alert upon the detection of said substance in the vicinity of said detector; and
    wherein said room monitoring system alerts the user via said remote monitoring device speaker.

11. The system of claim 10, further comprising:
    said room monitoring system comprising a remote camera, and said remote monitoring device comprising a video display for displaying a live video feed recorded by said remote camera;
    said event detector comprising a lighted region of said event detector housing configured to produce a visual alert upon the detection of said respective first and second broadband gas spectrums in the vicinity of said detector; and
    wherein said room monitoring system alerts the user via said remote monitoring device video display.

12. The system of claim 11, wherein said lighted region of said event detector housing comprises a graphical user interface.

13. The system of claim 1, further comprising:
    said event is selected from an event in the list comprising: fecal event, urine event and emesis event.

14. The system of claim 1, further comprising:
    said notification device comprising a Wi-Fi antenna for communicating with a mobile computing device, said mobile computing device including a graphical user interface (GUI), a communications antenna, and a microprocessor.

15. The system of claim 14, further comprising a Wi-Fi transceiver configured to receive communication data from said event detector and transmit said communication data to said mobile computing device.

* * * * *